US008546458B2

(12) United States Patent
Thompson et al.

(10) Patent No.: US 8,546,458 B2
(45) Date of Patent: Oct. 1, 2013

(54) PROCESS FOR TEXTURING MATERIALS

(75) Inventors: Jordan M. Thompson, Scotts Valley, CA (US); Alexei Goraltchouk, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/314,116

(22) Filed: Dec. 7, 2011

(65) Prior Publication Data

US 2012/0142798 A1    Jun. 7, 2012

Related U.S. Application Data

(60) Provisional application No. 61/420,683, filed on Dec. 7, 2010.

(51) Int. Cl.
*C08J 9/02*    (2006.01)
*C08L 83/04*   (2006.01)

(52) U.S. Cl.
USPC ............ 521/154; 521/79; 521/110; 521/122; 264/41; 264/51; 264/328.1

(58) Field of Classification Search
USPC .................. 521/154; 428/308.4; 264/45.6
See application file for complete search history.

(56) References Cited

U.S. PATENT DOCUMENTS

| | | |
|---|---|---|
| 2,805,208 A | 9/1957 | Roche |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras |
| 3,700,380 A | 10/1972 | Kitrilakis |
| 3,852,832 A | 12/1974 | McGhan |
| 3,934,274 A | 1/1976 | Hartley, Jr. |
| 4,034,751 A | 7/1977 | Hung |
| 4,157,085 A | 6/1979 | Austad |
| 4,231,979 A | 11/1980 | White |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,592,755 A | 6/1986 | Penton |
| 4,610,690 A | 9/1986 | Tiffamy |
| 4,636,213 A | 1/1987 | Pakiam |
| 4,643,733 A | 2/1987 | Becker |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl |
| 4,740,208 A | 4/1988 | Cavon |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan |
| 4,965,430 A | 10/1990 | Curtis |
| 4,969,899 A | 11/1990 | Cox, Jr. |
| 5,002,572 A | 3/1991 | Picha |

(Continued)

FOREIGN PATENT DOCUMENTS

| | | |
|---|---|---|
| EP | 0230672 | 8/1987 |
| EP | 0315814 | 5/1989 |

(Continued)

OTHER PUBLICATIONS

Harper, J.R.; Baumann Menko, T.M.; Nicholson, W. "Silicone Foams" Chapter 12 in Handbook of Polymeric Foams and Foam Technology. 2nd Ed. Ed. By D. Klempner and V. Sendijarevic. 2004. pp. 379-383.*

"Soma Foama(r) 15" by Smooth-on. Published on the web Jan. 5, 2008. Accessed Oct. 12, 2012 at www.smooth-on.com/tb/files/Soma_Foama_15.pdf.*

"Silc Pig(r) Pigments" by Smooth-on. Published on the web Jan. 15, 2010. Accessed Oct. 12, 2012 at www.smooth-on.com/tb/files/Silc_Pig_Pigments.pdf.*

"Product Profile" by NuSil. Copyright 2005.*

Jang, Hyeon Su. Convenient air purification nose mask. Patent No. KR 20100077105. SciFinder abstract. Accessed Sep. 24, 2012.*

Screen capture: Nusil homepage www.nusil.com accessed via internet archive wayback machine. Wayback date: Mar. 31, 2005. Accessed Oct. 9, 2012.*

(Continued)

*Primary Examiner* — Randy Gulakowski
*Assistant Examiner* — Christina Wales
(74) *Attorney, Agent, or Firm* — Linda Fox; Stephen Donovan; Debra Condino

(57) ABSTRACT

Provided are methods for making textured implantable materials made from two part RTV silicone foams and having a desired color or tone without the need for dyes or colorants.

13 Claims, No Drawings

(56) References Cited

U.S. PATENT DOCUMENTS

| | | |
|---|---|---|
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan |
| 5,026,394 A | 6/1991 | Baker |
| 5,034,422 A | 7/1991 | Triolo |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Petersen |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,459,167 A * | 10/1995 | Giesen ............................ 521/79 |
| 5,480,430 A | 1/1996 | Carlisle |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iverson |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| RE35,391 E | 12/1996 | Brauman |
| 5,589,176 A | 12/1996 | Seare |
| 5,605,693 A | 2/1997 | Seare |
| 5,607,473 A | 3/1997 | Weber-Unger |
| 5,624,674 A | 4/1997 | Seare, Jr. |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare, Jr. |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker |
| 5,935,164 A | 8/1999 | Iversen |
| 5,961,552 A | 10/1999 | Iversen |
| 5,964,803 A | 10/1999 | Iversen |
| 5,965,076 A | 10/1999 | Banks |
| 5,984,943 A | 11/1999 | Young |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. |
| 6,214,926 B1 | 4/2001 | Winn |
| 6,315,796 B1 | 11/2001 | Eaton |
| 6,387,133 B1 | 5/2002 | Perouse |
| 6,432,138 B1 | 8/2002 | Offray |
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson |
| 6,602,452 B2 | 8/2003 | Schuessler |
| 6,605,116 B2 | 8/2003 | Falcon |
| 6,638,308 B2 | 10/2003 | Corbitt, Jr. |
| 6,673,285 B2 | 1/2004 | Ma |
| 6,692,527 B1 | 2/2004 | Bellin |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt, Jr. |
| 6,900,055 B1 | 5/2005 | Fuller |
| 6,913,626 B2 | 7/2005 | McGhan |
| 6,916,339 B1 | 7/2005 | Missana |
| 6,921,418 B2 | 7/2005 | Ledergerber |
| 6,932,840 B1 | 8/2005 | Bretz |
| 7,081,135 B2 | 7/2006 | Smith et al. |
| 7,081,136 B1 | 7/2006 | Becker |
| 7,105,116 B2 | 9/2006 | Bellin |
| 7,169,180 B2 | 1/2007 | Brennan |
| 7,192,450 B2 | 3/2007 | Brauker |
| 7,244,270 B2 | 7/2007 | Lesh |
| 7,323,208 B2 | 1/2008 | Ma |
| 7,476,249 B2 | 1/2009 | Frank |
| 7,520,896 B2 | 4/2009 | Benslimane |
| 7,547,393 B2 | 6/2009 | Ramaswamy |
| 7,625,405 B2 | 12/2009 | Purkait |
| 7,632,228 B2 | 12/2009 | Brauker |
| 7,632,291 B2 | 12/2009 | Stephens |
| 7,641,688 B2 | 1/2010 | Lesh |
| 7,645,475 B2 | 1/2010 | Prewett |
| 8,202,317 B2 | 6/2012 | Becker |
| 8,313,527 B2 | 11/2012 | Powell et al. |
| 2002/0038147 A1 | 3/2002 | Miller |
| 2002/0193885 A1 | 12/2002 | Legeay |
| 2003/0036803 A1 | 2/2003 | McGhan |
| 2003/0093151 A1 | 5/2003 | Zhang |
| 2003/0105469 A1 | 6/2003 | Karmon |
| 2003/0205846 A1 | 11/2003 | Bellin |
| 2003/0208269 A1 | 11/2003 | Eaton |
| 2004/0010225 A1 | 1/2004 | Schuessler |
| 2004/0115241 A1 | 6/2004 | Calhoun |
| 2004/0127985 A1 | 7/2004 | Bellin |
| 2004/0143327 A1 | 7/2004 | Ku |
| 2004/0148024 A1 | 7/2004 | Williams |
| 2004/0153151 A1 | 8/2004 | Gonzales |
| 2004/0213986 A1 | 10/2004 | Kim |
| 2005/0055093 A1 | 3/2005 | Brennan |
| 2005/0070124 A1 | 3/2005 | Miller |
| 2005/0112169 A1 | 5/2005 | Brauker |
| 2005/0122169 A1 | 6/2005 | Watanabe |
| 2005/0196452 A1 | 9/2005 | Boyan et al. |
| 2005/0216094 A1 | 9/2005 | Prewett |
| 2006/0036266 A1 | 2/2006 | Sulamanidze et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2007/0093911 A1 | 4/2007 | Fricke |
| 2007/0104693 A1 | 5/2007 | Quijano |
| 2007/0104695 A1 | 5/2007 | Quijano |
| 2007/0116735 A1 | 5/2007 | Calhoun |
| 2007/0135916 A1 | 6/2007 | Maxwell |

| | | | | | | |
|---|---|---|---|---|---|---|
| 2007/0154525 | A1 | 7/2007 | Calhoun | WO | WO 00/24437 | 5/2000 |
| 2007/0190108 | A1 | 8/2007 | Datta et al. | WO | WO 2004/037318 | 5/2004 |
| 2007/0198085 | A1 | 8/2007 | Benslimane | WO | WO 2004/062531 | 7/2004 |
| 2008/0009830 | A1 | 1/2008 | Fujimoto | WO | 2006/133366 | 12/2006 |
| 2008/0071371 | A1 | 3/2008 | Elshout | WO | WO 2009/061672 | 5/2009 |
| 2008/0075752 | A1 | 3/2008 | Ratner | WO | WO 2009/110917 | 9/2009 |
| 2008/0154366 | A1 | 6/2008 | Frank | WO | WO 2011/094155 | 8/2011 |
| 2008/0241212 | A1 | 10/2008 | Moses | WO | WO 2011/097499 | 8/2011 |
| 2008/0268019 | A1 | 10/2008 | Badylak | | | |
| 2008/0312739 | A1 | 12/2008 | Agerup | | | |
| 2009/0045166 | A1 | 2/2009 | Li | | | |
| 2009/0082864 | A1 | 3/2009 | Chen | | | |
| 2009/0087641 | A1 | 4/2009 | Favis | | | |
| 2009/0093878 | A1 | 4/2009 | Glicksman | | | |
| 2009/0118829 | A1 | 5/2009 | Powell | | | |
| 2009/0125107 | A1 | 5/2009 | Maxwell | | | |
| 2009/0149953 | A1* | 6/2009 | Schuessler et al. ........... 623/8 | | | |
| 2009/0169716 | A1 | 7/2009 | Linhardt | | | |
| 2009/0198331 | A1 | 8/2009 | Kesten et al. | | | |
| 2009/0198332 | A1 | 8/2009 | Becker | | | |
| 2009/0198333 | A1 | 8/2009 | Becker | | | |
| 2010/0042211 | A1 | 2/2010 | Van Epps et al. | | | |
| 2010/0042212 | A1 | 2/2010 | Van Epps et al. | | | |
| 2010/0292790 | A1 | 11/2010 | Stroumpoulis et al. | | | |
| 2011/0054605 | A1 | 3/2011 | Becker | | | |
| 2011/0093069 | A1 | 4/2011 | Goraltchouk et al. | | | |
| 2011/0106249 | A1 | 5/2011 | Becker | | | |
| 2011/0117267 | A1 | 5/2011 | Powell et al. | | | |
| 2011/0184531 | A1 | 7/2011 | Goraltchouk et al. | | | |
| 2011/0196488 | A1 | 8/2011 | Goraltchouk et al. | | | |
| 2011/0196489 | A1 | 8/2011 | Van Epps et al. | | | |
| 2011/0276133 | A1 | 11/2011 | Liu et al. | | | |
| 2011/0276134 | A1 | 11/2011 | Manesis et al. | | | |
| 2011/0278755 | A1 | 11/2011 | Liu et al. | | | |
| 2011/0282444 | A1 | 11/2011 | Liu et al. | | | |
| 2011/0309541 | A1* | 12/2011 | Thompson et al. ........... 264/46.6 | | | |
| 2011/0313073 | A1 | 12/2011 | Goraltchouk et al. | | | |
| 2012/0004722 | A1 | 1/2012 | Goraltchouk et al. | | | |
| 2012/0041555 | A1 | 2/2012 | Manesis et al. | | | |
| 2012/0077010 | A1 | 3/2012 | Manesis et al. | | | |
| 2012/0077012 | A1 | 3/2012 | Liu et al. | | | |
| 2012/0077891 | A1 | 3/2012 | Liu et al. | | | |
| 2012/0101574 | A1 | 4/2012 | Goraltchouk et al. | | | |
| 2012/0321777 | A1 | 12/2012 | Stroumpoulis et al. | | | |
| 2013/0013062 | A1 | 1/2013 | Thompson et al. | | | |
| 2013/0023987 | A1 | 1/2013 | Liu et al. | | | |
| 2013/0032962 | A1 | 2/2013 | Liu et al. | | | |
| 2013/0053956 | A1 | 2/2013 | Powell et al. | | | |

FOREIGN PATENT DOCUMENTS

| | | |
|---|---|---|
| EP | 1532942 | 5/2005 |
| JP | 2003-062062 | 4/2003 |
| JP | 2007-029717 | 8/2007 |
| KR | 2010077105 A * | 7/2010 |
| WO | WO 98/10803 | 3/1998 |

OTHER PUBLICATIONS

Brauker et al., "Neovascularization of synthetic membranes directed by membrane microarchitecture", Journal of Biomedical Materials Research, 1995, pp. 1517-1524, vol. 29, John Wiley & Sons, Inc.

Brohim et al., "Early Tissue Reaction to Textured Breast Implant Surfaces", Anals of Plastic Surgery, 28(4): 354-362.

Sharkawy et al. "Engineering the tissue which encapsulates subcutaneous implants", II. Plasma—tissue exchange properties, 1998, pp. 586-597, John Wiley & Sons, Inc.

Alvarez, Sonia et al., "Synthesis of Macro/Mesoporous Silica and Carbon Monoliths by Using a Commercial Polyurethane Foam as Sacrificial Template", Materials Letters, 61, 2378-2381 (2007).

Barr, S. et al., "Current Implant Surface Technology: An Examination of Their Nanostructure and Their Influence on Fibroblast Alignment and Biocompatibility", Elastic, 2009, 9, 198-217.

Barnsley, Philip et al., "Textured Surface Breast Implants in the Prevention of Capsular Contracture Among Breast Augmentation Patients: A Meta-Analysis of Randomized Controlled Trials", Plastic and Reconstructive Surgery, 2006, 117(7), 2182-2190.

Inamed Aesthetics Brochure, Directions for Use Style 410 Silicone-Filled Breast Implants (2003).

Ma, Peter, "Scaffolds for tissue fabrication", Materials Today, 2004, 7, 30-40.

Mikes. Antonius et al., "Formation of Highly Porous Biodegradable Scaffolds for Tissue Engineering", Electronic Journal of Biotechnology, 2000, 3(2), 114-119.

Minami, Eliza et al., "The Composition and Behavior of Capsules Around Smooth and Textured Breast Implants in Pigs", Plastic and Reconstructive Surgery, 2006, 118940, 874-884.

Murphy, William et al., "Salt Fusion: An Approach to Improve Pore Interconnectivity Within Tissue Engineering Scaffolds", Tissue Engineering, vol. 8, Iss. 1, 2004.

Wei, Guobao et al., "Macroporous and Nanofibers Polymer Scaffolds and Polymer/bone-like Apatite Composite Scaffolds Generated by Sugar Spheres", Journal of I3iomedical Materials Research Part A, 2006, 306-315.

Zhang, Yuan et al., "Macroporous Alumina Monoliths Prepared by Filling Polymer Foams With Alumina Hydrosols", J. Mater Sci., 44, 931-938 (2009).

* cited by examiner

PROCESS FOR TEXTURING MATERIALS

This application claims priority to and the benefit of U.S. Provisional Patent Application No. 61/420,683, filed on Dec. 7, 2010, the entire disclosure of which is incorporated herein by this specific reference.

The present invention generally relates to textured materials, and more specifically relates to processes for making textured materials suitable for implantation.

Prostheses or implants for augmentation and/or reconstruction of the human body are well known. Capsular contracture is a complication associated with surgical implantation of prostheses, particularly with soft implants, and even more particularly, though certainly not exclusively, with fluid-filled breast implants.

Capsular contracture is believed to be a result of the immune system response to the presence of a foreign material in the body. A normal response of the body to the presence of a newly implanted object, for example a breast implant, is to form a capsule of tissue, primarily collagen fibers, around the implant. Capsular contracture occurs when the capsule begins to contract and squeeze the implant. This contracture can be discomforting or even extremely painful, and can cause distortion of the appearance of the augmented or reconstructed breast. The exact cause of contracture is not known. However, some factors may include bacterial contamination of the implant prior to placement, submuscular versus subgladular placement, and smooth surface implants versus textured surface implants, and bleeding or trauma to the area.

Surface texturing has been shown to reduce capsular contracture when compared to what are known as "smooth" surface implants. Current texturing techniques generally do not take into account the final color of the implant product.

During consultation with the physician, a patient considering breast reconstruction or augmentation is often shown various representative samples of breast implants. The patient may be provided the opportunity to view and handle the samples. A gel-filled implant may be compared side-by-side with a saline filled implant. Textured implants can be compared to so-called smooth-surface implants.

It is believed by the present inventors that other characteristics of the implant, for example, the tone or look, for example, even the color of a sample, may carry at least some value to a physician and/or patient.

Providing different tones or colors may be important for other reasons, for example, as a means of distinguishing different models or sizes of implants, each from the other.

There is still a need for new ways to manufacture textured materials for breast implants.

SUMMARY

Accordingly, the present invention provides a method of making an implantable, textured material of a desired appearance, specifically, a tone or color, without the use of addition of colorants or dyes. More specifically provided are methods for making textured implantable materials from two part RTV silicone foams and having a desired, preselected color or tone without the need for dyes or colorants.

In one aspect of the invention, the invention provides a process for creating a texture on the surface of materials using gas foaming and more specifically, to creating a texture having aesthetic properties, for example, using gas foaming.

The implantable materials can be made using gas foaming techniques. However, unlike conventional techniques, the present invention provides a means for creating implantable materials, for example, textured implantable materials useful as components of breast implants, which have a preselected tone or color, for example a preselected brown color tone, without the addition of dyes or colorants, using gas foaming techniques. The preselected brown color tone may be a brown tone, including, but not limited to, a brown tone, a buff brown tone and a bronze brown tone.

Generally, a base solution for the gas foam starts as a relatively dark material, and after a catalyst is added it becomes lighter with agitation. The inventors have found that by controlling agitation, subtly distinct darker or lighter toned materials can be achieved. The present invention provides methods for making implantable materials of a full range of skin tones.

For example, methods of making a material having a preselected color and suitable for implantation generally include the steps of providing a silicone base component, providing a catalyst for the base component, and combining the base component with the catalyst under preselected mixing conditions in order to achieve a polymerized silicone foam material having a preselected color. The preselected color is a color or tone selected from a range of brown color tones, including bronze-brown, buff-brown and brown.

DETAILED DESCRIPTION

The present invention provides methods of making a textured surface on implantable device, such as a breast implant, having a preselected or desired color or tone. The method generally comprises the steps of providing a silicone base component, providing a catalyst for the base component, combining the base component with the catalyst under preselected conditions in order to achieve a textured silicone material having a preselected color or tone.

In many embodiments of the invention, the method expressly excludes the addition of any colorant, dye or similar agent to achieve the desired color or tone. In some embodiments, the preselected color or tone correlates to a density of the silicone material.

Another advantage of the present invention is textured materials may be formed that promote tissue ingrowth. For example, the texture of the material may be open celled and somewhat crater-like.

Gas foaming involves the use of a mixture of two or more components, of which one is volatile under certain conditions and the other(s) form(s) the foam. Typically in silicone gas foaming a catalyst, a silicone polymer/monomer/oligomer and a foaming agent are used. When mixed in defined proportions the mixture undergoes polymerization and foam formation occurs. Mixing can be done by hand, with a power mixer, or any other standard mixing technique, this mixture can then be used with any other manufacturing process such as injection molding, dipping, casting, etc.

In accordance with an aspect of the invention, density of the foam is lowered, and thus, the tone of the foam may be made relatively lighter by increasing the speed of the agitation and by decreasing the amount of catalyst. Once the solution has been prepared it is poured on top of a base material, for example a silicone elastomer sheet. This surface will be textured by the foam. After polymerization is complete the foam is manually peeled away from the surface of the material. The gas foam solution polymerizes with the top layer of the silicone sheet and binds tightly to it. Excess foam may be removed, for example, by gentle scrubbing, leaving a textured surface layer remains on the base material. The peeling process is facilitated by the mechanical properties of the foam which create a weak-plane such that at least one cell layer remains on the base material. During multiple applications the weak-plane shifts upwards and facilitates the creation of multiple cell layers on the base material. As such, the peeling process of the excess foam is very simple, manual and can be introduced simply into any manufacturing process.

Typically, with the gas foaming technique, the foam forms a layer of skin on the surface. Skin is defined as a layer of porosity which is less than the bulk porosity of the remaining foam. Typically the skin is of sub-optimal porosity, often of no appreciable porosity. This event occurs due to collapse of the polymer at the surface during degassing and often limits the utility of the foam as is. Most manufacturing processes involve cutting off of the skin after the foaming is complete in order to create a foam sheet which is open-celled throughout the material. This greatly limits the geometry of foams produced by these methods. Typical foams are made into thick sheets, fixed to a revolving mandrel and sliced with a blade in a peeling like fashion in order to produce sheets of foam. This method is limited to producing foam in sheet form. The skin formation is undesirable in that it causes the foam to be non homogenous, mainly the skin has an undesirably low level of porosity. The described process allows for the creation of foams in any shape without a skin.

The present texturing process can be performed by dipping any material surface into a gas foaming solution, by pouring the solution on top of the surface, by spraying the solution onto a surface, or by other methods like injection molding. Using this method, the foam can be applied to any surface thereby texturing the target surface with one or more open celled layers.

One advantage of this process is that the gas foam texture can be applied to a surface rapidly. Once the gas foam solution has been prepared it can be applied to the sample surface. The foam only requires a few minutes to polymerize. After the polymerization is complete, the excess is removed and the textured layer remains adhered to the sample surface. The whole process can be performed in only a few minutes.

This process can also be repeated to thicken the layer of foam on the sample surface. Each layer that is added thickens the texture on the surface. Five layers are enough to create an open celled gas foam several millimeters thick on the surface of the sample. Each layer as it is applied polymerizes with the previous layer. When the excess is removed the layers remain. Due to this, multiple foam layers can be stacked upon each other to create the desired thickness for the sample. The porosity and density of each layer can also be altered by varying the agitation that the gas foam solution is mixed at. This can be used to create foams that have small pores at the proximity to the material being coated and gradually progress to larger pores with each additional layer. Alternatively a mix of small-large pore layers can be created; alternatively the pores on the material surface can be very big, decreasing in size with the application of each consecutive layer.

This process can also be used with surfaces of any geometry including surfaces which have already been textured by other means. For example the proposed technique can be applied to the Biocell surface to enhance the surface roughness. For this the sample first undergoes treatment to make the standard Biocell texture, followed by dipping the cured silicone shell in the gas foaming solution as described in the current invention.

Factors which can be varied in the current invention in order to achieve different results include: the amount of catalyst used, temperature of reactants, the intensity of stirring, the gas foam solution used, and how the sample is handled after the gas foam solution has been applied. The amount of catalyst used affects the porosity of the resulting foam, more catalyst increases porosity. In this manner the foam layer that is applied to the surface can be of varying geometries, starting out with small pores and going to large pores, or starting out with large pores and going to small pores, or of alternating pore sizes with each consecutive layer, etc. The catalyst also affects the working time required for the foam to harden. This affects the mechanical properties of the foam, such as elasticity and elongation at break. Typically, the more catalyst used, the worse the mechanical properties are. Controlling the temperature of the reactants affects the working time which affects the mechanical properties. Cooling the reactants increases the working time allowing polymerization to occur for longer than it otherwise would. The longer the polymerization time, the better the mechanical properties of the foam. The intensity of the stirring directly affects the density of the resulting foam. Increased stirring creates less dense foams. How the sample is handled after the gas foam solution has been applied directly affects the thickness of the resulting foam. A thick layer can be achieved by confining the sample to a mold, whereas a thin sample can be made by allowing the foam solution to run off of the sample. Alternatively, it may be possible to thin the sample by using processes like dipping, and rotating the sample after the foam solution has been applied.

The gas foam layer can be applied by any conventional coating technique such as dipping, casting, spraying unto a surface, etc. The removal of the foam can be manual peeling or automated, alternatively an adhesive surface can be used to facilitate the peeling process. In the manner described in this invention materials which textured surfaces can be created, the textures described can be from a single layer of open crater-like cells to an open celled foam of varying porosity and interconnectivity. The geometry of the texture is controlled by the geometry of the substrate, the microstructure of the texture is controlled by standard means of altering microstructures of all conventional gas foaming processes.

Hex code numbers given in the Examples are based on the hexadecimal code number system, which is a well known base-16 numbering system used to define colors. It is primarily used to define colors for web pages, but the inventors believe it is useful for identifying colors of the presently described foam-like materials as well. A hex number is written from 0-9 and then A-F. The first set represents the red hue, the second the green hue, and the third the blue. White is written as ff ff ff or #ffffff while black is 00 00 00 or #000000. Other examples are: Red=#ff0000, Green=#00ff00 and Blue=#0000ff. This is a color model that describes projected colors—colors as they are seen directly by our eyes, not reflected off of any surface and can be useful for defining the apparent brown color tones of the implantable materials described herein.

Color can also identifiable using the well known RGB color system (Red/Green/Blue) which is based on human perception of color. RGB colors can be converted to six digit hex code numbers and vice versa.

In the present invention, silicone foams can be made to have certain preselected colors, namely, various color shades in the brown color range.

In one embodiment, a process is provided for preparing, from a two part, RTV silicone foam (NuSil 2370) without added colors or dyes, a polymerized, porous, silicone foam having a bronze-brown color tone. For purposes of this disclosure, a bronze-brown color tone can be defined as a color having RGB color code values: R=about 184 to about 225, G=about 114 to about 140, and B=45 to about 55. Bronze color tones include, for example, color RGB code R-187, G-119, B-34 as well as color R-205, G-127, B-50.

The method comprises the steps of combining an uncolored, standard RTV silicone foam base (e.g. NuSil base R-2370) with its corresponding catalyst (e.g. NuSil catalyst R-2370), in a ratio of base to catalyst of about 100 ml base to 6 ml catalyst, and mixing the base and catalyst at a speed/agitation sufficient to create a foam having a viscosity of about 4300 mPas to about 4700 mPas, for example, about 4500 mPas. A molding surface can be dipped into this foam and allowed to polymerize. The resulting polymerized foam is removed from the molding surface has a bronze-brown color. The foam can then be used as a textured layer component on an inflatable breast implant, for example, as an outer surface of an inflatable, textured breast implant.

In another embodiment, a process for preparing a silicone foam is provided wherein the foam has a buff-brown color tone, that is, an RGB color code of RGB values: R=about 216 to about 264, G=about 198 to about 242, and B=180 to about 220. For example, buff-brown color tones include, for example, color RGB code R-238, G-238, B-187.

In this embodiment, the method comprises the steps of combining an uncolored, standard RTV silicone foam base (NuSil 2370) with its corresponding catalyst (NuSil 2370), and mixing the base and catalyst at a speed/agitation sufficient to create a foam having a viscosity of about 4800 mPas to about 5200 mPas, for example, about 5000 mPas. A molding surface can be dipped into the foam and allowed to polymerize. The resulting foam has a buff-brown color and is removed from the molding surface and used as a textured layer component on an inflatable breast implant.

In yet another embodiment, a process for preparing a silicone foam is provided wherein the foam has a brown color tone, that is, an RGB color code of RGB values: R=about 135 to about 165, G=about 68 to about 82, and B=0 to about 10. For example, brown color tones include, for example, color RGB code R-153, G-80, B-0.

In this embodiment, the method comprises the steps of combining an uncolored, standard RTV silicone foam base (NuSil 2380) with its corresponding catalyst (NuSil 2380), and mixing the base and catalyst at a speed/agitation sufficient to create a foam having a viscosity of about 3400 mPas to about 3800 mPas, for example, about 3600 mPas. A molding surface can be dipped into the foam and allowed to polymerize. The resulting foam has a brown color and is removed from the molding surface and used as a textured layer component on an inflatable breast implant.

The present invention further provides implantable materials useful as components of breast implants and having a desired color or tone and made by the methods described herein.

EXAMPLE 1

Process for Preparing a Silicone Foam Having a Bronze-Brown Color Tone

To prepare a bronze brown foam having a density of about 0.16 g/cm$^3$, a two-part RTV silicone foam, R-2370, available from NuSil Silicone Technology, was prepared by mixing 100 ml of R-2370 base with 6 ml of R-2370 catalyst. The sample was then placed in a homogenizer with a propeller attachment and vigorously stirred at about 50 rpm for about 30 seconds at which point the viscosity was approximately 4500 mPas. A mandrel was then dipped directly into the foaming solution such that it became fully coated with the solution. The mandrel was removed and the excess solution is allowed to drip off. The sample was then allowed polymerize and a foam formed upon the mandrel. The foam was then removed in a peeling process which involved manually, by hand, peeling off the foam using abrasion. A single, open celled, foam-like texture layer approximately 0.3 mm thick remained behind on the sample. This process was then repeated 4 more times to give an approximate texture thickness of 1.5 mm. The approximate foam density was 0.16 g/cm$^3$ and had a bronze brown color tone, RGB color code R-205, G-127, B-50 (hex code #CD7F32).

EXAMPLE 2

Process for Preparing a Silicone Foam Having a Buff-Brown Color Tone

A two-part RTV silicone foam, R-2370, available from NuSil Silicone Technology, was prepared by mixing 200 ml of R-2370 base with 12 ml of R-2370 catalyst. The sample was placed in a homogenizer with a propeller attachment and vigorously stirred at 100 rpm for 60 seconds at which point the viscosity was approximately 5000 mPas. A mandrel was then dipped directly into the foaming solution such that it was fully coated. The mandrel was removed and the excess solution was allowed to drip off. The sample was then allowed polymerize and a foam formed upon the mandrel. The foam was then removed in a peeling process which involves manually, by hand, peeling off the foam using abrasion. A single open celled foam like texture layer approximately 0.4 mm thick, remained behind on the sample. This process was then repeated 4 more times to give an approximate texture thickness of 2.0 mm. The approximate foam density was 0.11 g/cm$^3$ and had a buff brown color tone RGB color code R-240, G-220, B-200 (hex code #F0DCC82).

EXAMPLE 3

Process for Preparing a Silicone Foam Having a Brown Color Tone

A two-part RTV silicone foam, R-2380, available from NuSil Silicone Technology, was prepared by mixing 500 ml of R-2380 base with 30 ml of R-2380 catalyst. The sample was placed in a homogenizer with a propeller attachment and vigorously stirred at 200 rpm for 30 seconds at which point the viscosity was approximately 3600 mPas. A flat mandrel with a 1.0 mm layer of cured silicone was then dipped directly into the foaming solution such that it was fully submerged. The mandrel was removed and the excess solution was allowed to drip off. After 10 seconds a sheet of open celled 100 ppi polyurethane foam was then placed directly onto the top of the foam as it began to polymerize. The foam was then allowed polymerize and a form upon the mandrel. The foam was then removed in a peeling process which involved removing the polyurethane foam. A single open celled foam like texture layer approximately 0.5 mm thick remained behind on the sample. This process is then repeated 4 more times to give an approximate texture thickness of approximately 4.0 mm. The approximate foam density was 0.31 g/cm$^3$ and had a brown color tone and had a buff brown color tone RGB color code R-150, G-75, B-0 (hex code #964B00).

While this invention has been described with respect to various specific examples and embodiments, it is to be understood that the invention is not limited thereto and that it can be variously practiced within the scope of the invention.

What is claimed is:

1. A method of making a material having a preselected color and suitable for implantation in a mammal, the method comprising:
   providing a silicone base component;
   providing a catalyst for the base component;
   mixing the base component with the catalyst at about 200 rpm for about 30 seconds to achieve a foam solution; and
   allowing the foam solution to polymerize to achieve a polymerized silicone material having a brown tone with RGB color code values R=about 135 to about 165, G=about 68 to about 82, and B=0 to about 10.

2. The method of claim 1 that excludes the addition of any colorant, dye or similar agent.

3. A method of making a material having a preselected color and suitable for implantation in a mammal, the method comprising:
   providing a silicone base component;
   providing a catalyst for the base component;
   mixing the base component with the catalyst at about 100 rpm for about 60 seconds to achieve a foam solution; and
   allowing the foam solution to polymerize to achieve a polymerized silicone material having a buff brown tone having RGB color code values R=about 216 to about 264, G=about 198 to about 242, and B=180 to about 220.

4. The method of claim 3 wherein the foam solution has a viscosity of about 4800 mPas to about 5200 mPas.

5. The method of claim 3 wherein the foam solution has a viscosity of about 5000 mPas.

6. The method of claim 1 wherein the foam solution has a viscosity of between about 3400 mPas to about 3800 mPas.

7. The method of claim 1 wherein the foam solution has a viscosity of about 3600 mPas.

8. An implantable material useful as a component of a breast implant made by the method of claim 1.

9. An implantable material useful as a component of a breast implant made by a method of claim 3.

10. The method of claim 1 further comprising the step of applying the foam solution to a molding surface prior to the step of allowing the foam solution to polymerize.

11. The method of claim 1 further comprising the step of dipping a mandrel into the foam solution prior to the step of allowing the foam solution to polymerize.

12. The method of claim 3 further comprising the step of applying the foam solution to a molding surface prior to the step of allowing the foam solution to polymerize.

13. The method of claim 3 further comprising the step of dipping a mandrel into the foam solution prior to the step of allowing the foam solution to polymerize.

* * * * *

UNITED STATES PATENT AND TRADEMARK OFFICE
CERTIFICATE OF CORRECTION

Page 1 of 1

PATENT NO. : 8,546,458 B2
APPLICATION NO. : 13/314116
DATED : October 1, 2013
INVENTOR(S) : Jordan M. Thompson et al.

It is certified that error appears in the above-identified patent and that said Letters Patent is hereby corrected as shown below:

On the title page, (56), under "Other Publications", in column 2, line 3, delete "Ed. Ed." and insert -- Ed. --, therefor.

On the title page, (56), under "Other Publications", in column 2, line 5, delete "Foama(r)" and insert -- Foama® --, therefor.

On the title page, (56), under "Other Publications", in column 2, line 8, delete "Pig(r)" and insert -- Pig® --, therefor.

On title page 3, in column 2, under "Other Publications", line 34, delete "I3iomedical" and insert -- Biomedical --, therefor.

In the Specification

In column 1, line 27, delete "subgladular" and insert -- subglandular --, therefor.

Signed and Sealed this
Twenty-sixth Day of May, 2015

Michelle K. Lee
*Director of the United States Patent and Trademark Office*